United States Patent
Hrushka et al.

(10) Patent No.: US 11,504,263 B2
(45) Date of Patent: Nov. 22, 2022

(54) SANITARY STOMA SYSTEM AND METHOD

(71) Applicants: Garry Allan Hrushka, Edmonton (CA); Elizabeth Ann Harman Hrushka, Edmonton (CA)

(72) Inventors: Garry Allan Hrushka, Edmonton (CA); Elizabeth Ann Harman Hrushka, Edmonton (CA)

( * ) Notice: Subject to any disclaimer, the term of this patent is extended or adjusted under 35 U.S.C. 154(b) by 562 days.

(21) Appl. No.: 16/132,261

(22) Filed: Sep. 14, 2018

(65) Prior Publication Data
US 2020/0085608 A1 Mar. 19, 2020

(51) Int. Cl.
*A61F 5/44* (2006.01)
*A61F 5/441* (2006.01)
*A61F 5/443* (2006.01)

(52) U.S. Cl.
CPC ............ *A61F 5/4401* (2013.01); *A61F 5/441* (2013.01); *A61F 5/443* (2013.01)

(58) Field of Classification Search
CPC .. A61F 5/44; A61F 5/445; A61F 5/443; A61F 5/441; A61F 5/4401; A61F 2005/4402; A61F 13/15; A61F 13/20; A61F 13/2011; A61F 13/206; A61F 13/2062; A61F 13/2065; A61F 13/2068; A61F 13/2071; A61F 13/2094; A61F 13/2097; A61F 13/55145; A47K 2010/3206; A47L 13/16; B32B 2555/00; B32B 2555/02; Y10T 428/15; Y10S 604/904; A61L 28/0053
See application file for complete search history.

(56) References Cited

U.S. PATENT DOCUMENTS

| | | | |
|---|---|---|---|
| 2,064,586 A | 12/1936 | Boser | |
| 3,726,277 A * | 4/1973 | Hirschman | ......... A61F 13/2051 604/359 |
| 4,121,589 A | 10/1978 | McDonnell | |
| 4,187,850 A * | 2/1980 | Gust | ....................... A61F 5/445 604/338 |
| 4,209,009 A * | 6/1980 | Hennig | ................. A61F 2/0018 600/30 |
| 4,238,059 A | 12/1980 | Caraway et al. | |
| 4,258,704 A | 3/1981 | Hill | |
| 4,661,101 A * | 4/1987 | Sustmann | ............... A61L 15/46 604/360 |

(Continued)

FOREIGN PATENT DOCUMENTS

| | | |
|---|---|---|
| CA | 2163248 | 12/1994 |
| DE | 2634642 A1 | 2/1977 |
| EP | 0644745 | 3/1995 |

*Primary Examiner* — Adam Marcetich
(74) *Attorney, Agent, or Firm* — Runyan Law; Charles Runyan

(57) ABSTRACT

A sanitary stoma system including at least eight absorbent sheets, with each of the sheets including absorbent plies. The plurality of absorbent sheets is arranged in a linear fashion and removably connected into a roll. The outermost absorbent sheet includes an adhesive such that the sanitary stoma system is configured into a stable roll useful for being placed upon a stoma of a user to absorb and contain bodily fluids excreted from the stoma, which may include urine or feces. Preferably, the sanitary stoma system is packaged in multiples of three and the sanitary stoma system is affixable to an abdomen of the user, configured to absorb bodily excretions.

20 Claims, 5 Drawing Sheets

(56) References Cited

U.S. PATENT DOCUMENTS

| | | | | |
|---|---|---|---|---|
| 4,787,895 A * | 11/1988 | Stokes | A61F 13/206 | 604/358 |
| 4,865,594 A | 9/1989 | Thomas | | |
| 4,950,223 A | 8/1990 | Silvanov | | |
| 4,966,595 A * | 10/1990 | Meringola | A61F 13/44 | 206/63.3 |
| 4,979,947 A * | 12/1990 | Berman | A61F 5/445 | 604/369 |
| 4,981,465 A | 1/1991 | Ballan et al. | | |
| 5,688,260 A * | 11/1997 | Blanton | A61F 13/2051 | 604/11 |
| 5,972,456 A * | 10/1999 | Esquivel | B32B 29/00 | 428/154 |
| 6,359,191 B1 * | 3/2002 | Rusch | A61F 13/206 | 604/364 |
| 6,409,709 B1 * | 6/2002 | Recto | A61F 5/445 | 604/338 |
| 6,569,081 B1 * | 5/2003 | Nielsen | A61F 2/0009 | 600/32 |
| 6,936,305 B1 * | 8/2005 | Biagiotti | B65H 18/00 | 118/235 |
| 8,821,465 B2 | 9/2014 | Hakuna et al. | | |
| 9,757,270 B2 | 9/2017 | Carrubba | | |
| 2002/0026177 A1 * | 2/2002 | Lochte | A61F 13/2051 | 604/385.17 |
| 2002/0068918 A1 * | 6/2002 | Durel-Crain | A61F 13/202 | 604/385.18 |
| 2002/0077611 A1 | 6/2002 | Dyck et al. | | |
| 2003/0208180 A1 * | 11/2003 | Fuchs | A61F 13/206 | 604/385.17 |
| 2004/0030305 A1 | 2/2004 | Sakamoto | | |
| 2004/0192642 A1 * | 9/2004 | Yang | A61P 31/04 | 514/54 |
| 2004/0260257 A1 * | 12/2004 | Ciok | A61F 5/445 | 604/332 |
| 2005/0148920 A1 * | 7/2005 | Addison | A61F 13/00995 | 602/46 |
| 2005/0209574 A1 * | 9/2005 | Boehringer | A61F 13/36 | 604/289 |
| 2005/0256482 A1 * | 11/2005 | Minoguchi | A61F 13/2085 | 604/385.17 |
| 2006/0252008 A1 * | 11/2006 | Muller | A61F 13/36 | 433/136 |
| 2007/0066924 A1 | 3/2007 | Hopman et al. | | |
| 2008/0269698 A1 | 10/2008 | Alexander et al. | | |
| 2010/0130907 A1 * | 5/2010 | Linkel | A61F 13/2065 | 604/11 |
| 2010/0145292 A1 * | 6/2010 | Mayer | A61F 13/2051 | 604/337 |
| 2010/0243499 A1 * | 9/2010 | Slayton | B65D 75/527 | 206/440 |
| 2010/0256545 A1 * | 10/2010 | Aali | A61F 13/0203 | 604/304 |
| 2011/0079671 A1 * | 4/2011 | Wojcik | B65H 18/22 | 242/532.2 |
| 2011/0220128 A1 * | 9/2011 | Steinberg | A61F 13/2011 | 128/887 |
| 2013/0160259 A1 * | 6/2013 | McDaniel | A61F 13/2031 | 28/120 |
| 2014/0005627 A1 * | 1/2014 | McDaniel | A61F 13/206 | 604/385.17 |
| 2014/0115846 A1 * | 5/2014 | Tomsovic | A61F 13/206 | 28/118 |
| 2015/0335495 A1 * | 11/2015 | Wigder | A61F 13/2011 | 604/363 |
| 2015/0366727 A1 * | 12/2015 | Lepke | A61F 13/12 | 604/377 |
| 2016/0113810 A1 | 4/2016 | Hakuna et al. | | |
| 2017/0204304 A1 * | 7/2017 | Yu | C08L 5/06 | |
| 2017/0280946 A1 * | 10/2017 | Weisang | B65H 19/286 | |
| 2018/0273329 A1 * | 9/2018 | Nagubadi | B65H 18/04 | |
| 2020/0054476 A1 * | 2/2020 | Miller | A61F 5/445 | |
| 2021/0127909 A1 * | 5/2021 | Stoeffler | B65H 18/28 | |

\* cited by examiner

SANITARY STOMA SYSTEM AND METHOD

BACKGROUND OF THE INVENTION

The following includes information that may be useful in understanding the present disclosure. It is not an admission that any of the information provided herein is prior art nor material to the presently described or claimed inventions, nor that any publication or document that is specifically or implicitly referenced is prior art.

TECHNICAL FIELD

The present invention relates generally to the field of surgery of the existing art and more specifically relates to means and methods for collecting body fluids or waste material.

RELATED ART

In anatomy, a natural stoma is any opening in the body, for example, the mouth. Any hollow or semi-hollow organ can be manipulated into an artificial stoma as necessary. This includes the esophagus, stomach, duodenum, ileum, colon, pleural cavity, ureters, urinary bladder, and/or kidney. One well-known form of an artificial stoma is a ostomy, which is a surgically created opening in the intestine which allows the removal of feces from the body (bypassing the rectum) to drain into a pouch or other similar collection device.

Other stoma may include an opening in the urinary system, which may be referred to as a urostomy. A urostomy is a surgical procedure that creates a stoma (artificial opening) for the urinary system. A urostomy is made to for urinary diversion in cases where drainage of urine through the bladder and urethra is not possible. Some possible uses may be for bladder removal or obstructions.

The location where the waste exits the body is considered the stoma. For greatest success and to minimize negative effects, it is preferable to perform this procedure as low down in the tract as possible, as this allows the maximum amount of natural digestion to occur before eliminating waste from the body. The stoma is usually covered with a removable pouch system that collects and contains the discharge for later disposal. Modern pouching systems enable most individuals to resume normal activities and lifestyles after surgery, often with no outward physical evidence of the stoma or its pouching system.

A major limitation with the artificial stoma system is that the pouch must be removed and replaced and/or emptied once full. Also, the location at which the pouch attaches to the user's body requires a barrier, which is a gasket-like device to seal the stoma site. Often time the removal and replacement of the pouch or barrier provides for leakage from the stoma the stoma is required to maintain sterility. Therefore, a suitable solution is desired.

U.S. Pat. No. 4,121,589 to Roy Edward McDonnel relates to an ostomy appliance. The described ostomy appliance includes an attachment portion having an aperture adapted to register with an opening in the body of a patient and having adhesive on one face adapted to secure the attachment portion to the body of the patient surrounding the opening, the attachment portion being provided on the opposite face thereof with structure for securing a cap member in sealing relationship thereto over the aperture; and a cap member comprising a generally concave body member of rigid or semi-rigid material, the body member containing absorbent material for absorbing drainage and/or discharge from the opening and being provided with structure engaging the attachment portion for securing said cap member to said attachment means. The appliance may further include an absorber member adapted to be inserted into the opening through the aperture in the attachment portion, the absorber member comprising a generally tubular absorption and storage member having inner and outer walls of fluid pervious material, the inner and outer walls being separated by absorbent material, and a flange at one end of the tubular member to retain the absorber member in position in the opening on securing the cap member to the attachment portion.

SUMMARY OF THE INVENTION

In view of the foregoing disadvantages inherent in the known means and methods for collecting body fluids or waste material art, the present disclosure provides a novel sanitary stoma system and method. The general purpose of the present disclosure, which will be described subsequently in greater detail, is to provide an efficient and effective sanitary stoma system and method.

A sanitary stoma system is disclosed herein. The sanitary stoma system includes at least eight absorbent sheets, with each of the sheets including a plurality of absorbent plies. The plurality of absorbent sheets are arranged in a linear fashion and removably connected end to end such that the plurality of absorbent sheets is assembled together in a wound roll.

Each of the absorbent sheets is preferably each at least 1½" in width, with the width being perpendicular to the linear arrangement of an adjacent absorbent sheet and the absorbent sheets are preferably square in shape. The outermost absorbent sheet includes an adhesive such that the sanitary stoma system is configured into a stable roll useful for being placed upon a stoma of a user to absorb and contain bodily fluids excreted from the stoma. Preferably, the sanitary stoma system is packaged in multiples of three and the sanitary stoma system is affixable to an abdomen of the user, configured to absorb urine.

Also, the sanitary stoma system is preferably disposable via a sanitary means (e.g., flushable) and is further biodegradable. The sanitary stoma system includes a lanyard configured to allow the user to easily remove the sanitary stoma system. Preferably, the sanitary stoma system includes a cotton material configured to improve absorbency as well as a chemical treatment to reduce odors produced from the stoma and stoma excretions. Further, the sanitary stoma system is preferably hypoallergenic and sterile, configured to reduce instances of inflammation during use.

According to another embodiment, a method of using a sanitary stoma system is also disclosed herein. The method of using a sanitary stoma system includes a first step, providing a sanitary stoma system; a second step, removing a medical barrier from a stoma site; a third step, placing the sanitary stoma system upon a stoma site of a user (the sanitary stoma system absorbing bodily fluids from the stoma site); a fourth step, cleaning an area adjacent to the stoma site; a fifth step, placing a medical barrier upon the stoma site; a sixth step, removing the sanitary stoma system from the stoma site; and a seventh step, affixing an ostomy bag to the medical barrier.

For purposes of summarizing the invention, certain aspects, advantages, and novel features of the invention have been described herein. It is to be understood that not necessarily all such advantages may be achieved in accordance with any one particular embodiment of the invention.

Thus, the invention may be embodied or carried out in a manner that achieves or optimizes one advantage or group of advantages as taught herein without necessarily achieving other advantages as may be taught or suggested herein. The features of the invention which are believed to be novel are particularly pointed out and distinctly claimed in the concluding portion of the specification. These and other features, aspects, and advantages of the present invention will become better understood with reference to the following drawings and detailed description.

BRIEF DESCRIPTION OF THE DRAWINGS

The figures which accompany the written portion of this specification illustrate embodiments and methods of use for the present disclosure, a sanitary stoma system and method, constructed and operative according to the teachings of the present disclosure.

The various embodiments of the present invention will hereinafter be described in conjunction with the appended drawings, wherein like designations denote like elements.

DETAILED DESCRIPTION

As discussed above, embodiments of the present disclosure relate to means and methods for collecting body fluids or waste material and more particularly to a sanitary stoma system and method as used to improve the sanitation of the changing of a barrier and ostomy bag while reducing instances of leakage during the changing process.

Generally, a sanitary stoma system is useful to control and contain bodily waste from a stoma during the changing of a barrier, skin guard and pouch (i.e., bag). The sanitary stoma system provides a sterile device to contain the waste during the changing procedure with a disposable device to reduce instances of contamination. The device can be placed over the stoma site 'hands-free' (e.g., without the need to hold). The sanitary stoma system covers and protects the affected area and prevents leakage during the changing process as the system absorbs and discharge from the site.

Referring now more specifically to the drawings by numerals of reference, there is shown in FIGS. 1A-4, various views of a sanitary stoma system 100.

Figure 1A:
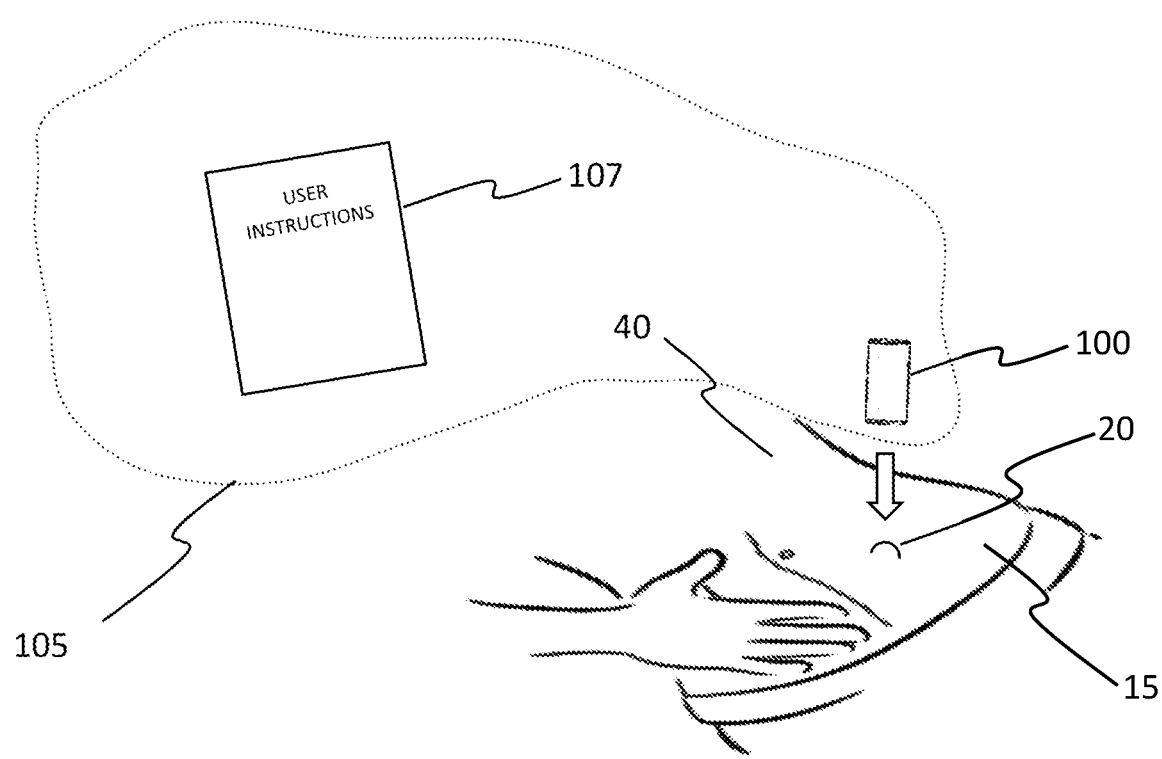
FIG. 1A is a perspective view of the sanitary stoma system during an 'in-use' condition, according to an embodiment of the disclosure.
Figure 1B:
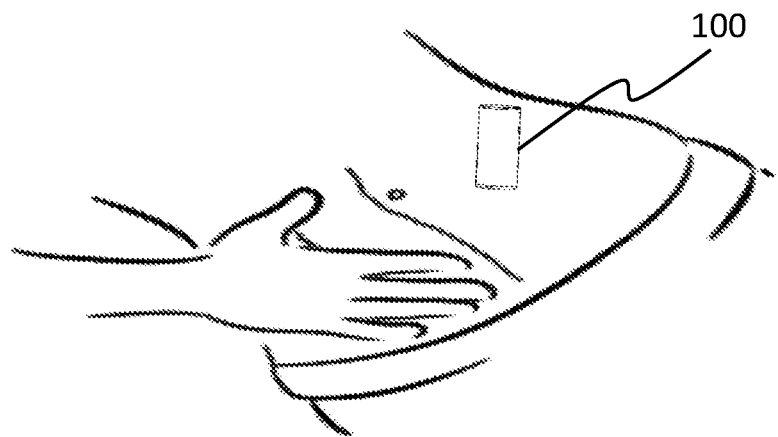
FIG. 1B is an additional perspective view of the sanitary stoma system during an 'in-use' condition, according to an embodiment of the disclosure.

FIGS. 1A and 1B show sanitary stoma system 100 during an 'in-use' condition 50, according to an embodiment of the present disclosure. Here, sanitary stoma system 100 may be beneficial for use by user 40 to provide a device useful for covering stoma 20 of user 40 in a sanitary condition while absorbing materials discharged from stoma 20 during maintenance of stoma 20 (e.g., when a skin barrier and/or pouch is changed).

Figure 2:
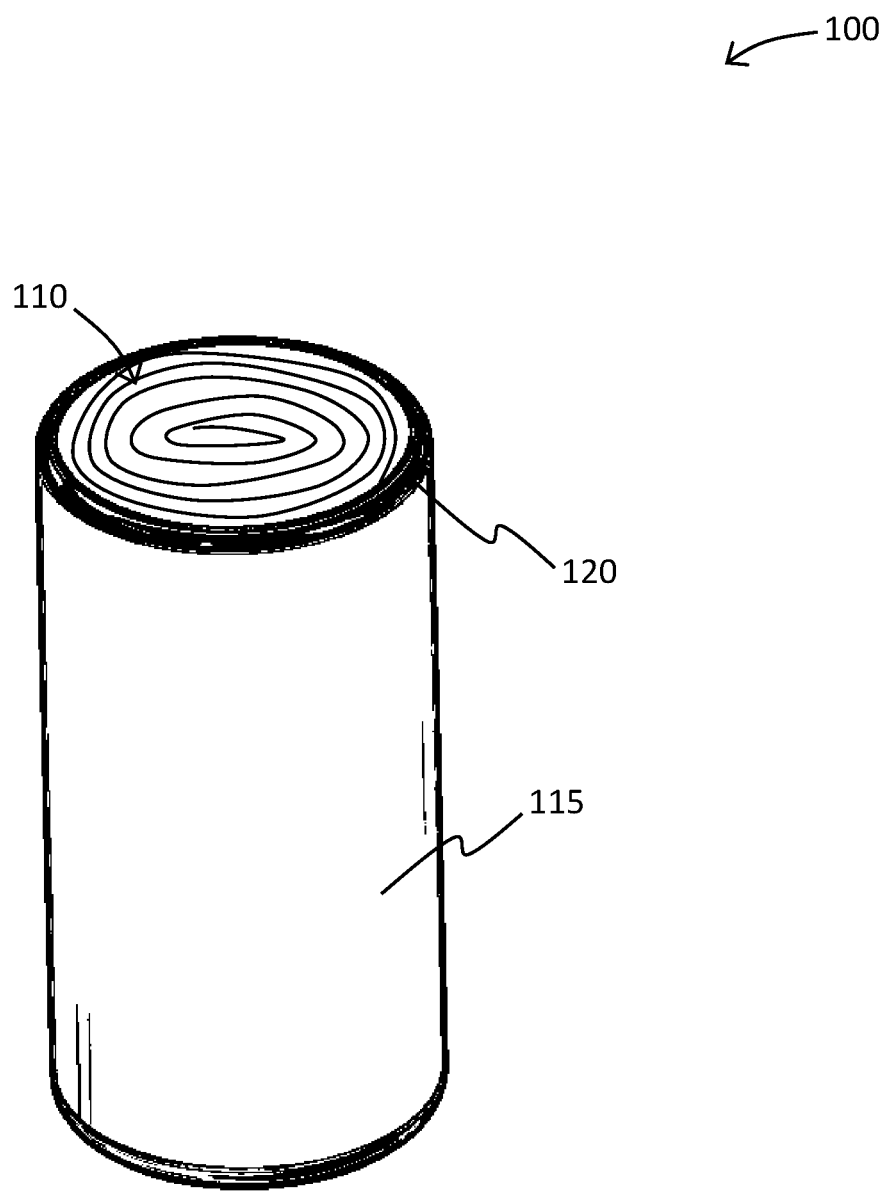
FIG. 2 is a top-front perspective view of the sanitary stoma system of FIGS. 1A and 1B, according to an embodiment of the present disclosure.
Figure 3:
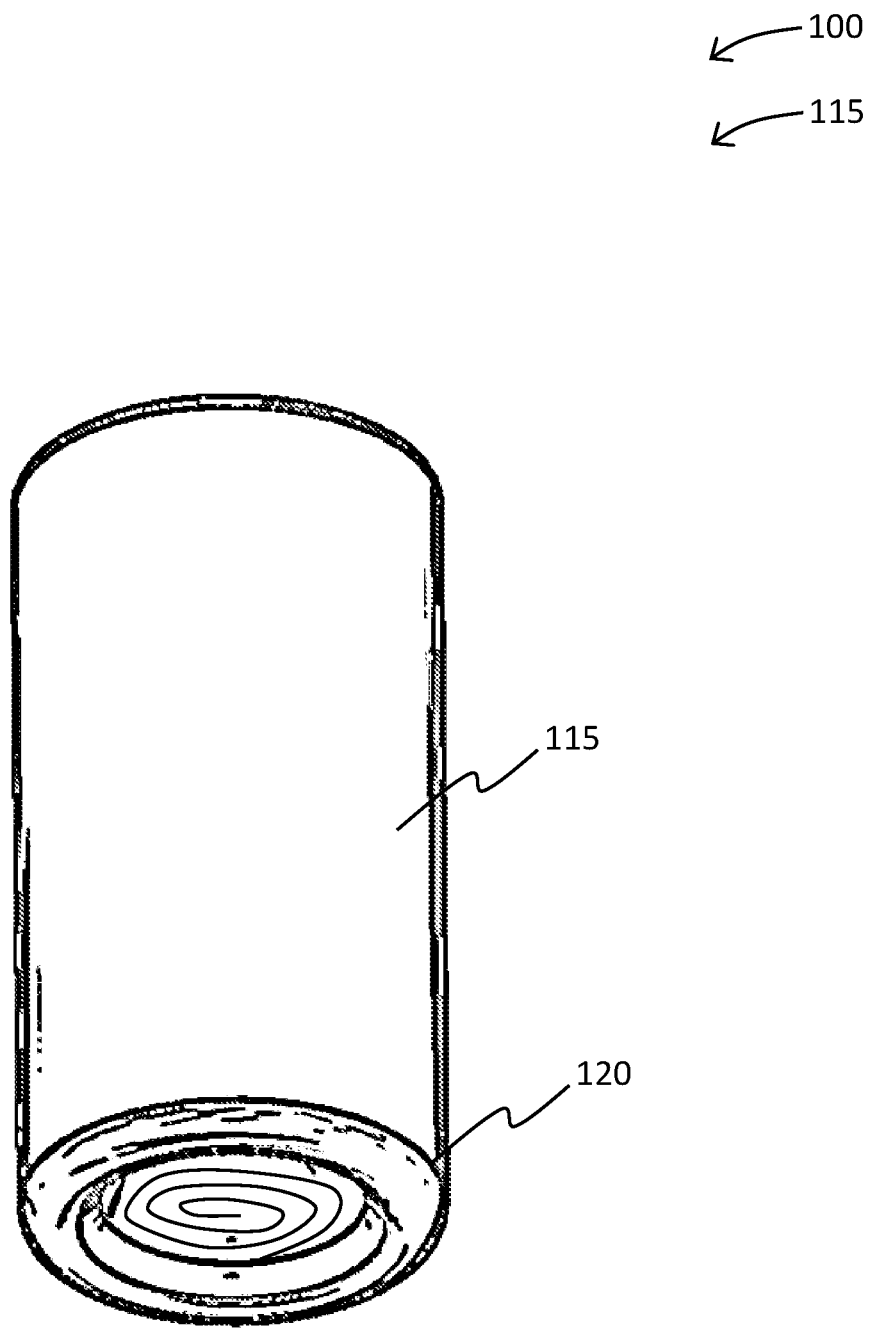
FIG. 3 is a bottom-front perspective view of the sanitary stoma system of FIGS. 1A and 1B, according to an embodiment of the present disclosure.
Figure 4:
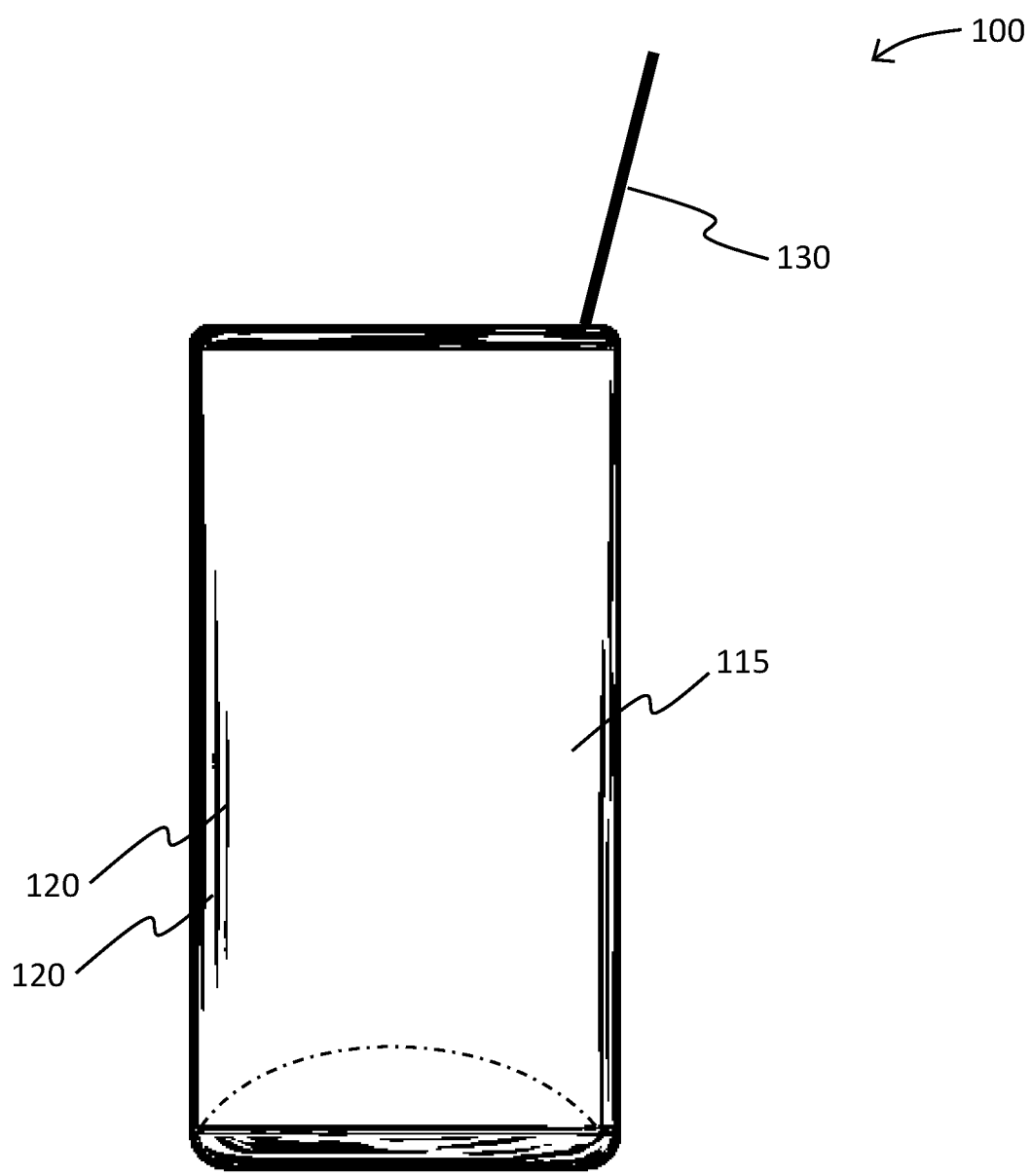
FIG. 4 is a front perspective view of the sanitary stoma system of FIGS. 1A and 1B, according to an embodiment of the present disclosure.

As illustrated in FIGS. 1A-4, sanitary stoma system 100 may include at least eight absorbent sheets 110, where absorbent sheets 110 may include a plurality of absorbent plies 120, where plurality of absorbent sheets 110 may be arranged in a linear fashion, removably connected end to end (e.g., may be a continuous linear roll with perforations between each sheet). Also, plurality of absorbent sheets 110 may be assembled in wound roll 115 (as shown in FIGS. 2-4). Upon reading this specification, it should be appreciated that, under appropriate circumstances, considering such issues as user preferences, design preference, structural requirements, marketing preferences, cost, available materials, technological advances, etc., other arrangements such as, for example, different amounts of plies, shapes of plies, and overall configuration, etc., may be sufficient.

Absorbent sheets 110 may each be at least 1½" in width, with the width being perpendicular to the linear arrangement of an adjacent absorbent sheet 110; and absorbent sheets 110 may be square in shape. Other shapes and sizes may be used depending upon user preferences and manufacturability.

An outermost absorbent sheet 110 may include an adhesive (which may be upon an edge of outermost absorbent sheet 110) such that sanitary stoma system 100 may be configured into a stable roll useful for being placed upon stoma 20 of user 40 to absorb and contain bodily fluids excreted from stoma 20. Sanitary stoma system 100 may also include lanyard 130 configured to allow user 40 to easily remove sanitary stoma system 100 without physically touching absorbent sheets 110 and/or wound roll 115.

Embodiments of sanitary stoma system 100 may be affixable to abdomen of user 40, configured to absorb urine. Additional embodiments of sanitary stoma system 100 may be affixable to an abdomen 15 of user 40, configured to absorb feces. Further embodiments of sanitary stoma system 100 may be affixable to a backside of user 40. Locations of use for sanitary stoma system 100 may include further locations, dependent upon the medical condition and needs of user 40.

According to one embodiment, sanitary stoma system 100 may be arranged as a kit 105. In particular, sanitary stoma system 100 may further include a set of instructions 107. The instructions 107 may detail functional relationships in relation to the structure of, sanitary stoma system 100 such that sanitary stoma system 100 can be used, maintained, or the like, in a preferred manner.

Sanitary stoma system 100 may be disposable via a sanitary system (e.g., sewer system, flushable, etc.), in embodiments. Alternate embodiments may include sanitary stoma system 100 which may be washable and reusable. Further embodiments may include sanitary stoma system 100 which may be biodegradable.

Sanitary stoma system 100 may include a cotton material configured to improve absorbency and/or may include a cellulose fiber material configured to increase structural strength. Sanitary stoma system 100 may also, or alternately, include synthetic fibers configured to increase structural strength. Sanitary stoma system 100 may also include a chemical treatment to reduce odors produced from stoma 20. Sanitary stoma system 100 may be packaged in multiples of three, in embodiments. Some embodiments may include alternate packaging arrangements.

Sanitary stoma system 100 may be hypoallergenic and/or sanitary stoma system 100 may sterile, configured to reduce inflammation during use. Sanitary stoma system 100 may include an anti-bacterial treatment configured to reduce instances of infection during use. Those with ordinary skill in the art will now appreciate that upon reading this specification and by their understanding the art of means and methods for collecting body fluids or waste material as described herein, methods of use and maintenance of means and methods for collecting body fluids or waste material will be understood by those knowledgeable in such art.

Figure 5:
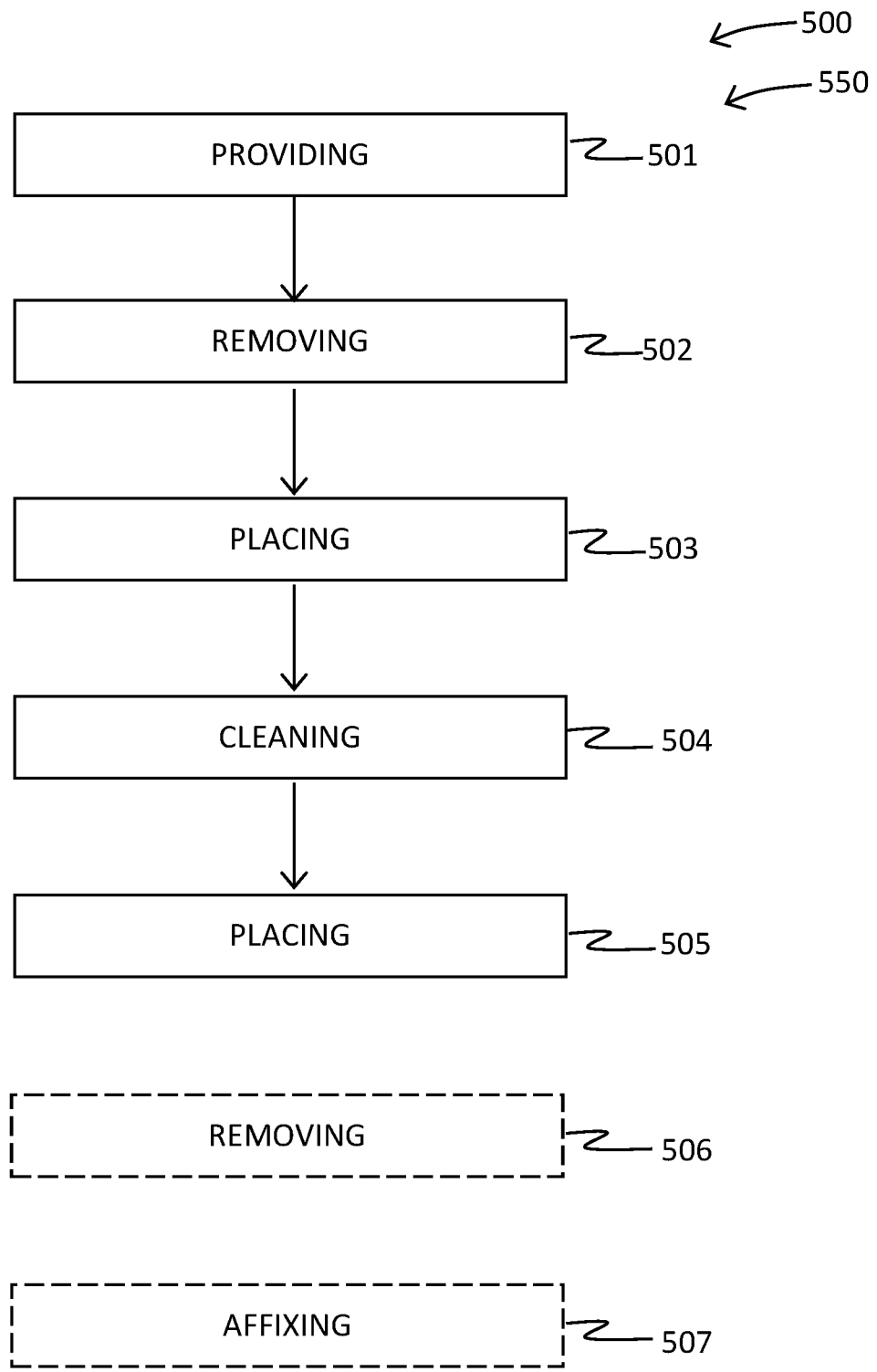
FIG. 5 is a flow diagram illustrating a method of using a sanitary stoma system, according to an embodiment of the present disclosure.

FIG. 5 is a flow diagram illustrating method of using a sanitary stoma system 500, according to an embodiment of the present disclosure. In particular, method of using a sanitary stoma system 500 may include one or more components or features of sanitary stoma system 100 as described above. As illustrated, method of using a sanitary stoma system 500 may include the steps of: step one 501, providing sanitary stoma system; step two 502, removing a medical barrier from stoma 20 site; step three 503, placing sanitary stoma system 100 upon stoma 20 site of user 40, sanitary stoma system 100 absorbing bodily fluids from stoma 20 site; step four 504, cleaning the area adjacent to stoma 20 site; step five 505, placing a medical barrier upon stoma 20 site; step six 506, removing sanitary stoma system 100 from stoma 20 site; and step seven 507, removing sanitary stoma system 100 from stoma 20 site.

It should be noted that step six 506 and step seven 507 are optional steps and may not be implemented in all cases. Optional steps of method of use 500 are illustrated using dotted lines in FIG. 5 so as to distinguish them from the other steps of method of use 500. It should also be noted that the steps described in the method of use can be carried out in many different orders according to user preference.

The use of "step of" should not be interpreted as "step for", in the claims herein and is not intended to invoke the provisions of 35 U.S.C. § 112(f). It should also be noted that, under appropriate circumstances, considering such issues as design preference, user preferences, marketing preferences, cost, structural requirements, available materials, technological advances, etc., other method of using a sanitary stoma system (NOTE: e.g., different step orders within above-mentioned list, elimination or addition of certain steps, including or excluding certain maintenance steps, etc.), are taught herein.

The embodiments of the invention described herein are exemplary and numerous modifications, variations and rearrangements can be readily envisioned to achieve substantially equivalent results, all of which are intended to be embraced within the spirit and scope of the invention. Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application.

What is claimed is new and desired to be protected by Letters Patent is set forth in the appended claims:

1. A sanitary stoma system, the system comprising:
   at least eight absorbent sheets, said sheets including a plurality of absorbent plies, said plurality of absorbent sheets arranged in a linear fashion removably connected end to end;
   wherein said absorbent sheets are each at least 3.81 cm (1½") in width, said width being perpendicular to said linear arrangement of an adjacent absorbent sheet; wherein said absorbent sheets are square in shape; and wherein said plurality of absorbent sheets are assembled in a wound roll of an appropriate size to match a stoma of a user to absorb and contain bodily fluids excreted from said stoma.

2. The sanitary stoma system of claim 1, wherein said sanitary stoma system is disposable via a sanitary system.

3. The sanitary stoma system of claim 1, wherein said sanitary stoma system is washable and reusable.

4. The sanitary stoma system of claim 1, wherein said sanitary stoma system includes a lanyard configured to allow said user to easily remove said sanitary stoma system.

5. The sanitary stoma system of claim 1, wherein said sanitary stoma system includes a cotton material configured to improve absorbency.

6. The sanitary stoma system of claim 1, wherein said sanitary stoma system includes a cellulose fiber material configured to increase structural strength.

7. The sanitary stoma system of claim 1, wherein said sanitary stoma system includes synthetic fibers configured to increase structural strength.

8. The sanitary stoma system of claim 1, wherein said sanitary stoma system includes a chemical treatment to reduce odors produced from said stoma.

9. The sanitary stoma system of claim 1, wherein said sanitary stoma system is affixable to an abdomen of said user and configured to absorb urine.

10. The sanitary stoma system of claim 1, wherein said sanitary stoma system is affixable to an abdomen of said user and configured to absorb feces.

11. The sanitary stoma system of claim 1, wherein said sanitary stoma system is affixable to a backside of said user.

12. The sanitary stoma system of claim 1, wherein said sanitary stoma system is biodegradable.

13. The sanitary stoma system of claim 1, wherein said sanitary stoma system is hypoallergenic, configured to reduce instances of inflammation during use.

14. The sanitary stoma system of claim 1, wherein said sanitary stoma system is sterile and configured to reduce instances of inflammation during use.

15. The sanitary stoma system of claim 1, wherein said sanitary stoma system includes an antibacterial treatment configured to reduce instances of infection during use.

16. The sanitary stoma system of claim 1, wherein said sanitary stoma system is packaged in multiples of three.

17. The sanitary stoma system of claim 1, further comprising an adhesive along an edge of the outer sheet sufficient to maintain the structure of the roll during application to a stoma.

18. The sanitary stoma system of claim 17, not comprising a separate cap around the adhesive.

19. A method comprising the steps of:
   opening a package containing a sanitary stoma system comprising a wound roll of absorbent sheets removably connected end to end lengthwise, each sheet having absorbent plies;
   removing a used medical barrier from a stoma site of a user;
   placing the wound roll upon the stoma site without placing a separate cap around the wound roll;
   cleaning an area adjacent to the stoma site; and
   placing a fresh medical barrier upon the stoma site.

20. The method of claim 19, further comprising the steps of:
   removing the wound roll from the stoma site; and
   affixing an ostomy bag to the medical barrier.

* * * * *